United States Patent
Martin et al.

(10) Patent No.: US 10,460,434 B2
(45) Date of Patent: Oct. 29, 2019

(54) METHOD OF DEFECT DETECTION AND SYSTEM THEREOF

(71) Applicant: APPLIED MATERIALS ISRAEL LTD., Rehovot OT (IL)

(72) Inventors: Limor Martin, Ramat-Gan (IL); Elad Cohen, Beer Sheva (IL); Eyal Neistein, Herzliya (IL); Moshe Amzaleg, Beer Sheva (IL)

(73) Assignee: Applied Materials Israel Ltd., Rehovot (IL)

( * ) Notice: Subject to any disclaimer, the term of this patent is extended or adjusted under 35 U.S.C. 154(b) by 242 days.

(21) Appl. No.: 15/683,726

(22) Filed: Aug. 22, 2017

(65) Prior Publication Data

US 2019/0066291 A1    Feb. 28, 2019

(51) Int. Cl.
| | | |
|---|---|---|
| G06T 7/00 | (2017.01) | |
| G06T 5/00 | (2006.01) | |
| H01L 21/67 | (2006.01) | |
| G01N 21/956 | (2006.01) | |
| H01L 21/66 | (2006.01) | |

(52) U.S. Cl.
CPC ..... *G06T 7/0008* (2013.01); *G01N 21/95607* (2013.01); *G06T 5/002* (2013.01); *G06T 7/001* (2013.01); *H01L 21/67288* (2013.01); *H01L 22/12* (2013.01); *G06T 2207/10061* (2013.01); *G06T 2207/20224* (2013.01); *G06T 2207/30148* (2013.01)

(58) Field of Classification Search
None
See application file for complete search history.

(56) References Cited

U.S. PATENT DOCUMENTS

| | | | |
|---|---|---|---|
| 6,539,106 B1 * | 3/2003 | Gallarda | G01R 31/307 382/149 |
| 9,704,234 B2 | 7/2017 | Huang et al. | |
| 2004/0240723 A1 * | 12/2004 | Sakai | G06T 7/001 382/141 |
| 2004/0264760 A1 * | 12/2004 | Ishikawa | G01N 21/95607 382/145 |

(Continued)

FOREIGN PATENT DOCUMENTS

WO    2009/026358 A1    2/2009

*Primary Examiner* — Kim Y Vu
*Assistant Examiner* — Nathan J Bloom
(74) *Attorney, Agent, or Firm* — Lowenstein Sandler LLP

(57) ABSTRACT

There are provided system and method of detecting defects on a specimen, the method comprising: capturing a first image from a first die and obtaining one or more second images; receiving: i) a first set of predefined first descriptors each representing a type of DOI, and ii) a second set of predefined second descriptors each representing a type of noise; generating at least one difference image based on difference between pixel values of the first image and pixel values derived from the second images; generating at least one third image, comprising: computing a value for each given pixel of at least part of the at least one difference image based on the first and second sets of predefined descriptors, and surrounding pixels centered around the given pixel; and determining presence of defect candidates based on the at least one third image and a predefined threshold.

20 Claims, 4 Drawing Sheets

(56) References Cited

U.S. PATENT DOCUMENTS

| | | | |
|---|---|---|---|
| 2005/0179910 A1* | 8/2005 | Bartov | G01N 21/9501 356/503 |
| 2006/0193506 A1* | 8/2006 | Dorphan | G01N 21/9501 382/145 |
| 2009/0016595 A1 | 1/2009 | Peterson et al. | |
| 2012/0163698 A1* | 6/2012 | Michelsson | G01N 21/9501 382/141 |
| 2019/0026879 A1* | 1/2019 | Batikoff | G06T 7/001 |
| 2019/0066292 A1* | 2/2019 | Pomeranz | G06T 7/0008 |
| 2019/0094155 A1* | 3/2019 | Honda | G01N 21/8806 |

* cited by examiner

METHOD OF DEFECT DETECTION AND SYSTEM THEREOF

TECHNICAL FIELD

The presently disclosed subject matter relates, in general, to the field of defect detection, and more specifically, to methods and systems of detecting defects on a specimen.

BACKGROUND

Current demands for high density and performance associated with ultra large scale integration of fabricated devices require submicron features, increased transistor and circuit speeds, and improved reliability. As semiconductor processes progress, pattern dimensions such as line width, and other types of critical dimensions, are continuously shrunken. Such demands require formation of device features with high precision and uniformity, which, in turn, necessitates careful monitoring of the fabrication process, including frequent and detailed inspections of the devices while they are still in the form of semiconductor wafers.

The term "specimen" used in this specification should be expansively construed to cover any kind of wafer, masks, and other structures, combinations and/or parts thereof used for manufacturing semiconductor integrated circuits, magnetic heads, flat panel displays, and other semiconductor-fabricated articles.

The term "inspection" used in this specification should be expansively construed to cover any kind of detection and/or classification of defects in a specimen provided by using non-destructive inspection tools or inspection machines. By way of non-limiting example, the inspection process can include generating an inspection recipe and/or runtime scanning (in a single or in multiple scans), reviewing, measuring and/or other operations provided with regard to the specimen or parts thereof using the same or different inspection tools. Note that, unless specifically stated otherwise, the term "inspection" or its derivatives used in this specification are not limited with respect to resolution or size of inspection area.

A variety of non-destructive inspection tools includes, by way of non-limiting example, scanning electron microscopes (SEM), tunneling electron microscope (TEM), atomic force microscopes (AFM), optical inspection tools, etc.

Inspection generally involves generating some output (e.g., images, signals, etc.) for a wafer by directing light or electrons to the wafer and detecting the light or electrons from the wafer. Once the output has been generated, defect detection is typically performed by applying defect detection method and/or algorithm to the output. Most often, the goal of inspection is to provide high sensitivity to defects of interest while suppressing detection of nuisance and noise on the wafer.

A reference die image is often used for detecting defects. For example, in a die-to-die method, the presence or absence of a defect in a location is checked by comparing the pattern at the desired location in an inspected die with the pattern of the same location in another die, e.g., a previously inspected die. A disadvantage of using a reference die image for inspection is that various noises that are caused by different variations, such as, e.g., process variations, mechanical and electrical variations, etc., may be imposed during inspection. In some cases certain noises can interfere with defect detection and decrease the sensitivity of defect detection. Such noises should be considered and disregarded, otherwise detection sensitivity and integrity are hindered. For instance, in a relatively noisy environment, the real defects can be buried within noise and cannot be duly detected. This challenge increases as the design rules shrinks and more and more potential defects are detected.

There is a need in the art for improving the performance of detecting defects of interest.

GENERAL DESCRIPTION

In accordance with certain aspects of the presently disclosed subject matter, there is provided computerized system of detecting defects on a specimen, the system comprising: an inspection unit configured to capture a first image from a first die of the specimen and obtain one or more second images; an I/O interface configured to receive: i) a first set of predefined first descriptors each indicative of pixel value distribution in a first image block associated therewith and representing a type of defect of interest (DOI), and ii) a second set of predefined second descriptors each indicative of pixel value distribution in a second image block associated therewith and representing a type of noise; and a processing unit operatively connected to the inspection unit and the I/O interface, the processing unit comprising a memory and a processor operatively coupled thereto, wherein: the processing unit is configured to generate at least one difference image based on difference between pixel values of the first image and pixel values derived from the one or more second images; generate at least one third image corresponding to the at least one difference image, comprising, computing a value for each given pixel of at least part of the at least one difference image based on the first set of predefined first descriptors, the second set of predefined second descriptors, and surrounding pixels centered around the given pixel; and determine presence of defect candidates in the first image based on the at least one third image and a predefined threshold.

In addition to the above features, the system according to this aspect of the presently disclosed subject matter can comprise one or more of features (i) to (xvii) listed below, in any desired combination or permutation which is technically possible:

(i). The one or more second images can include one or more images captured from one or more second dies, or a simulated image representing the first die.

(ii). The computing can comprise computing a value for the given pixel in accordance with a predefined formula related to a first set of block operations each using a predefined first descriptor and at least part of the surrounding pixels and a second set of block operations each using a predefined second descriptor and at least part of the surrounding pixels.

(iii). The predefined formula can be a polynomial formula.

(iv). The block operations can be convolution operations.

(v). The first image block can have a size of a predefined number of pixels, the second image block can have the same size as the first image block, and the computing can comprise:

a. selecting, on the at least one difference image, a surrounding image block each constituted by surrounding pixels centered around the given pixel, the surrounding image block having the same size as the first image block, and b. computing a value for the given pixel in accordance with a predefined formula related to a first set of block operations each using a predefined first descriptor and the surrounding pixels and a second set of block operations each using a predefined second descriptor and the surrounding pixels.

(vi). The first image block can have a first size of a first predefined number of pixels, the second image block can have a second size of a second predefined number of pixels, and the computing can comprise:

i. selecting, on the at least one difference image, a first surrounding image block and a second surrounding image block constituted by surrounding pixels centered around the given pixel, the first surrounding image block having the same size as the first image block, the second surrounding image block having the same size as the second image block; and ii. computing a value for the given pixel in accordance with a predefined formula related to a first set of block operations each using a predefined first descriptor and surrounding pixels in the first surrounding image block and a second set of block operations each using a predefined second descriptor and surrounding pixels in the second surrounding image block.

(vii). The inspection unit can be configured to obtain a defect map representative of one or more locations of initial defect candidates on the specimen, and capture one or more first images from the one or more locations, and for each location, obtain one or more second images. The generating at least one difference image and generating at least one third image are performed for each first image, giving rise to one or more third images corresponding to the one or more first images. And the determining presence of defect candidates can be based on the one or more third images and the predefined threshold.

(viii). The noise can include a non-DOI defect.

(ix). The type of noise can include detector noise.

(x). The detector noise can be Spontaneous Emission (SE) noise.

(xi). The specimen can be selected from a group comprising: a wafer, a reticle, a mask, an integrated circuit and a flat panel display.

(xii). Each of the first set of predefined first descriptors can be indicative of pixel value distribution in a two-dimensional kernel selected from a group comprising: a Gaussian kernel, a polynomial kernel, a uniform kernel, and an exponential kernel.

(xiii). Each of the second set of predefined second descriptors can be indicative of pixel value distribution in a two-dimensional kernel selected from a group comprising: a Gaussian kernel, a polynomial kernel, a uniform kernel, and an exponential kernel.

(xiv). The first set of predefined first descriptors and the second set of predefined second descriptors can be defined based on pixel value distribution learnt from previous inspection results.

(xv). The at least one difference image can be generated based on a corrected difference between pixel values of the first image and pixel values derived from the one or more second images, giving rise to at least one corrected difference image so as to compensate noises occurred in the first image, and wherein the at least one third image is generated based on the at least one corrected difference image.

(xvi). The predefined threshold can be determined based on a required amount of defect candidates.

(xvii). The processing unit can be further configured to send information of the defect candidates to a review machine for further inspection, and obtain information of defects detected by the review machine to be used for refining definition of the first set of predefined first descriptors and the second set of predefined second descriptors.

In accordance with another aspect of the presently disclosed subject matter, there is provided a computerized method of detecting defects on a specimen, the method comprising: capturing, by an inspection unit, a first image from a first die of the specimen and obtaining one or more second images; receiving, by an I/O interface: i) a first set of predefined first descriptors each indicative of pixel value distribution in a first image block associated therewith and representing a type of defect of interest (DOI), and ii) a second set of predefined second descriptors each indicative of pixel value distribution in a second image block associated therewith and representing a type of noise; generating, by a processing unit operatively connected to the inspection unit and the I/O interface, at least one difference image based on difference between pixel values of the first image and pixel values derived from the one or more second images; generating, by the processing unit, at least one third image corresponding to the at least one difference image, comprising, computing a value for each given pixel of at least part of the at least one difference image based on the first set of predefined first descriptors, the second set of predefined second descriptors, and surrounding pixels centered around the given pixel; and determining, by the processing unit, presence of defect candidates in the first image based on the at least one third image and a predefined threshold.

This aspect of the disclosed subject matter can comprise one or more of features (i) to (xvii) listed above with respect to the system, mutatis mutandis, in any desired combination or permutation which is technically possible.

In accordance with another aspect of the presently disclosed subject matter, there is provided a non-transitory computer readable storage medium tangibly embodying a program of instructions that, when executed by a computer, cause the computer to perform a method of detecting defects on a specimen, the method comprising: capturing, by an inspection unit, a first image from a first die of the specimen and obtaining one or more second images; receiving, by an I/O interface: i) a first set of predefined first descriptors each indicative of pixel value distribution in a first image block associated therewith and representing a type of defect of interest (DOI), and ii) a second set of predefined second descriptors each indicative of pixel value distribution in a second image block associated therewith and representing a type of noise; generating, by a processing unit operatively connected to the inspection unit and the I/O interface, at least one difference image based on difference between pixel values of the first image and pixel values derived from the one or more second images; generating, by the processing unit, at least one third image corresponding to the at least one difference image, comprising, computing a value for each given pixel of at least part of the at least one difference image based on the first set of predefined first descriptors, the second set of predefined second descriptors, and surrounding pixels centered around the given pixel; and determining, by the processing unit, presence of defect candidates in the first image based on the at least one third image and a predefined threshold.

This aspect of the disclosed subject matter can comprise one or more of features (i) to (xvii) listed above with respect to the system, mutatis mutandis, in any desired combination or permutation which is technically possible.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "capturing", "receiving", "generating", "determining", "representing", "computing", "selecting", "obtaining", "sending", "obtaining", "refining", "detecting", or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, the defect detection system and parts thereof as well as the processing circuitry therein disclosed in the present application.

The terms "non-transitory memory" and "non-transitory storage medium" used herein should be expansively construed to cover any volatile or non-volatile computer memory suitable to the presently disclosed subject matter.

The term "defect" used in this specification should be expansively construed to cover any kind of abnormality or undesirable feature or void formed on or within a specimen.

The term "design data" used in the specification should be expansively construed to cover any data indicative of hierarchical physical design (layout) of a specimen. Design data can be provided by a respective designer and/or can be derived from the physical design (e.g. through complex simulation, simple geometric and Boolean operations, etc.). Design data can be provided in different formats as, by way of non-limiting examples, GDSII format, OASIS format, etc. Design data can be presented in vector format, grayscale intensity image format or otherwise.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination. In the following detailed description, numerous specific details are set forth in order to provide a thorough understanding of the methods and apparatus.

Figure 1:
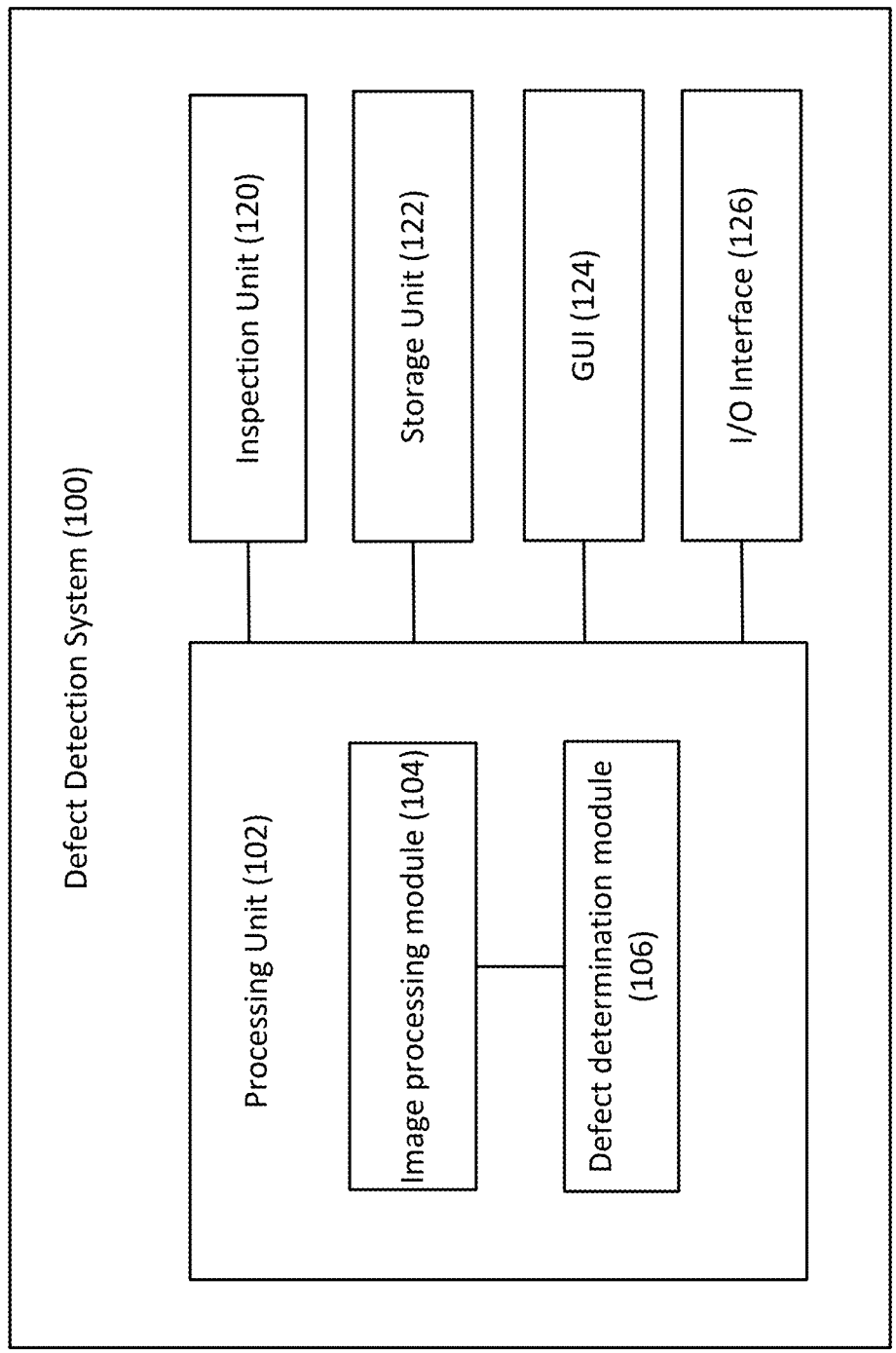
FIG. 1 illustrates a block diagram of a defect detection system in accordance with certain embodiments of the presently disclosed subject matter.

Bearing this in mind, attention is drawn to FIG. 1 illustrating a block diagram of a defect detection system in accordance with certain embodiments of the presently disclosed subject matter.

The defect detection system 100 illustrated in FIG. 1 can be used for detecting defects on a specimen. As aforementioned, the term "specimen" used in this specification should be expansively construed to cover any kind of wafer, masks, and other structures, combinations and/or parts thereof used for manufacturing semiconductor integrated circuits, magnetic heads, flat panel displays, and other semiconductor-fabricated articles. According to certain embodiments, the specimen used herein can be selected from a group comprising: a wafer, a reticle, a mask, an integrated circuit and a flat panel display (or at least a part thereof).

Defect detection system 100 can comprise, or be operatively connected to, an inspection unit 120. The term "inspection unit" used herein should be expansively construed to cover any inspection tools or inspection machines that can be used in inspection-related processes including, by way of non-limiting example, imaging, scanning (in a single or in multiple scans), sampling, reviewing, measuring, classifying and/or other processes provided with regard to the specimen or parts thereof. The present disclosure is not limited by the inspection technology. By way of example, the inspection unit can be an optical inspection tool or E-beam inspection tool. Non-limiting examples of inspection tools include scanning electron microscope (SEM), Tunneling Electron Microscope (TEM), optical metrology (OCD) or Atomic Force Microscopy (AFM)), etc.

In certain embodiments, inspection can employ a two phase "scanning and review" procedure. During the first phase, the surface of a specimen is inspected at high-speed and relatively low-resolution. In the first phase a defect map is produced to show suspected locations on the specimen having high probability of a defect. During the second phase the suspected locations are more thoroughly analyzed. In some cases both phases can be implemented by the same inspection tool, and in some other cases these two phases are implemented by different inspection tools.

The inspection unit 120 can be configured to capture a first image (hereinafter also referred to as inspection image) from a first die of the specimen (e.g., by scanning the specimen). The inspection unit 120 can also be configured to obtain one or more second images (hereinafter also referred to as reference images), as will be described in details below with reference to FIG. 2.

According to certain embodiments, the Defect detection system 100 can comprise a hardware-based I/O interface 126 which is operatively connected to the inspection unit and the processing unit. The I/O interface can be configured to receive, (for example, from a user such as, e.g., a semiconductor manufacturer, or from a third party system communicatively connected thereto): i) a first set of predefined first descriptors (also referred to as first descriptors) each indicative of pixel value distribution in a first image block associated therewith and representing a type of defect of interest (DOI), and ii) a second set of predefined second descriptors (also referred to as second descriptors) each indicative of pixel value distribution in a second image block associated therewith and representing a type of noise.

The term "Defect of interest (DOI)" used herein refers to any real defects that are of the user's interest to be detected. For instance, any "killer" defects that may cause yield loss can be indicated as DOI, as in comparison to nuisance type of defects which are also real defects but do not impact yield and therefore should be ignored. DOI can be of various types, and each type of DOI can be represented by a predefined first descriptor indicative of pixel value distribution in a first image block associated therewith.

The term "noise" used herein should be expansively construed to include any unwanted or not-of-interest defects (also referred to as non-DOI, or nuisance), as well as random noises that are caused by different variations (e.g., process variation, color variation, mechanical and electrical variations, etc.) during inspection and carry no useful information. Noises can also be of various types. Each type of noise can be represented by a predefined second descriptor indicative of pixel value distribution in a second image block associated therewith.

According to certain embodiments, the Defect detection system 100 can comprise, or be operatively connected to a storage unit 122. The storage unit 122 can be configured to store any data necessary for operating Defect detection system 100, e.g., data related to input and output of system 100, as well as intermediate processing results generated by system 100. By way of example, the storage unit 122 can be configured to store images produced by the inspection unit 120 and/or derivatives thereof. Accordingly, the first image and one or more second images can be retrieved from the storage unit 122 and provided to the Defect detection system 100 for further processing. Additionally or alternatively, the storage unit 122 can be configured to store the first set of predefined first descriptors and second set of predefined second descriptors as described above, which can be retrieved therefrom and provided to system 100 as input.

Defect detection system 100 comprises a processing unit 102 operatively connected to the inspection unit 120. The processing unit 102 is a processing circuitry that is configured to provide all processing necessary for operating system 100 which is further detailed with reference to FIGS. 2-3. Processing unit 102 comprises a processor (not shown separately) and a memory (not shown separately). The processor of processing unit 102 can be configured to execute several functional modules in accordance with computer-readable instructions implemented on a non-transitory computer-readable memory comprised in the processing unit. Such functional modules are referred to hereinafter as comprised in the processing unit 102.

Functional modules comprised in the processing unit 102 can include an image processing module 104 and a defect determination module 106, which are operatively connected with each other. The image processing module 104 can be configured to generate at least one difference image based on difference between pixel values of the first image and pixel values derived from the one or more second images. The image processing module 104 can be further configured to generate at least one third image (hereinafter also referred to as grade image) corresponding to the at least one difference image. The generation of the at least one third image can comprise computing a value for each given pixel of at least part of the at least one difference image based on the first set of predefined first descriptors, the second set of predefined second descriptors, and surrounding pixels centered around the given pixel.

Upon the at least one third image being generated, the defect determination module 106 can be configured to determine presence of defect candidates in the first image based on the at least one third image and a predefined threshold. Operations of the system 100, processing unit 102 and the functional modules therein will be further detailed with reference to FIGS. 2-3.

In some embodiments, the Defect detection system 100 can optionally comprise a computer-based Graphical user interface (GUI) 124 which is configured to enable user-specified inputs related to system 100. For instance, the user can be presented with a visual representation of the specimen (for example, by a display forming part of GUI 124). The user may be provided, through the GUI, with options of defining certain operation parameters. The user may also view the detection results on the GUI.

According to certain embodiments, Defect detection system 100 can be implemented as stand-alone computer(s) and can be operatively connected to the inspection unit 120 to operate in conjunction therewith. In such cases system 100 can receive, through an I/O interface, either directly or via one or more intermediate systems, the inspection images and reference images from the inspection unit and perform the image processing and defect detection based on the received images. In some embodiments, the Defect detection system 100 may be hosted by an inspection tool (e.g., the inspection unit 120) and may be configured to operate in conjunction with the hosting inspection tool and optionally with additional inspection tools. In some embodiments, system 100 may be integrated with an inspection tool (e.g., the inspection unit 120)—in such embodiments, components of the system 100 may form part of the inspection unit 120. For example, processing unit 102 and storage unit 122 may form part of the processing unit and storage, respectively, of the inspection unit 120; and the GUI (not shown in FIG. 1) of the inspection tool 120 may function as GUI 124.

Defect detection system 100 can be further configured to provide, via an I/O interface, the detection results (or part thereof) to a storage system which may be the same as the storage unit 122, or may be in addition or in lieu of the storage unit 122. The results can also be sent to any of the inspection tool(s) and/or review tool(s) and/or any other external system, and/or to the GUI 124 for rendering the results.

Those versed in the art will readily appreciate that the teachings of the presently disclosed subject matter are not bound by the system illustrated in FIG. 1; equivalent and/or modified functionality can be consolidated or divided in another manner and can be implemented in any appropriate combination of software with firmware and hardware.

It is noted that the system illustrated in FIG. 1 can be implemented in a distributed computing environment, in which the aforementioned functional modules shown in FIG. 1 can be distributed over several local and/or remote devices, and can be linked through a communication network. It is further noted that although the inspection unit 120, storage unit 122, and GUI 124 are illustrated as being part of the system 100 in FIG. 1, in some other embodiments, at least part of the aforementioned units can be implemented as being external to system 100 and can be configured to operate in data communication with system 100 via I/O interface. As aforementioned, in some cases, system 100 can be implemented as stand-alone computer(s) to be used in conjunction with the inspection unit 120. Alternatively, the respective functions of system 100 can, at least partly, be integrated with one or more inspection units 120.

Figure 2:
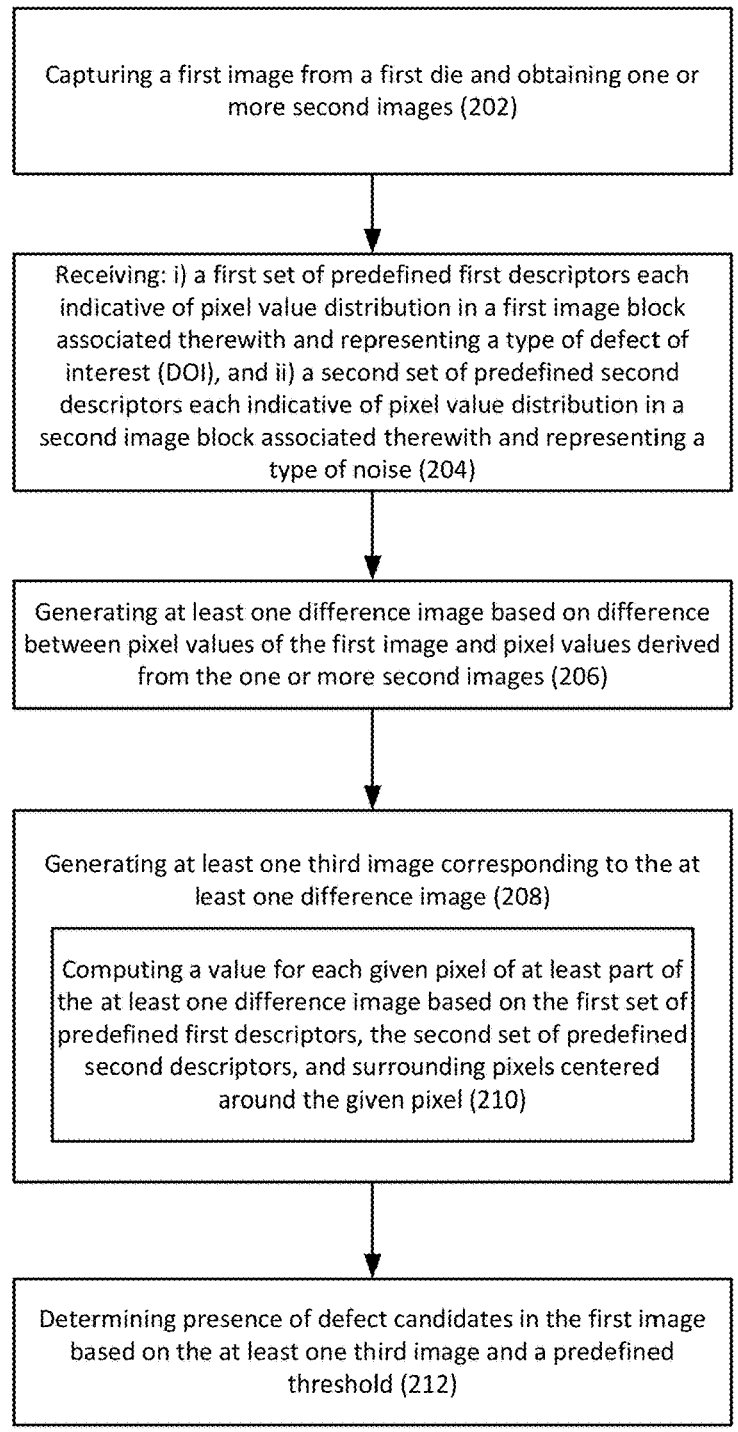
FIG. 2 illustrates a generalized flowchart of detecting defects on a specimen in accordance with certain embodiments of the presently disclosed subject matter.

Referring to FIG. 2, there is illustrated a generalized flowchart of detecting defects on a specimen in accordance with certain embodiments of the presently disclosed subject matter.

For purpose of illustration only, certain embodiments of the following description are provided with respect to wafers. Embodiments are, likewise, applicable to other types, sizes and representations of specimen.

A first image (i.e., inspection image) can be captured (202) (e.g., by the inspection unit 120 as illustrated in FIG. 1) from a first die of the specimen and one or more second images (i.e., reference images) can be obtained. The first die refers to the die to be inspected. An inspection image of a die can be captured by any inspection tool that is capable of imaging a die. By way of example, the inspection image can be captured by scanning the specimen or part thereof using an optical inspection tool or E-beam inspection tool, of which non-limiting examples are described above with reference to FIG. 1.

In some embodiments, the one or more second images can include one or more images captured (e.g., by the inspection unit 120) from one or more second dies of the same specimen. In some other embodiments, the one or more second images can include one or more images captured from one or more dies of another specimen (e.g., a second specimen that is different from the present specimen but shares the same design data). By way of example, in Die-to-History (D2H) inspection methodology, the first image can be captured from the present specimen at a present time (e.g., t=t'), and the one or more second images can include one or more previous images captured from one or more dies on a second specimen at a baseline time (e.g., a previous time t=0). In some further embodiments, the one or more second images can include at least one simulated image representing the first die. By way of example, a simulated image can be generated based on design data (e.g., CAD data) of the first die.

In some cases, although there are provided multiple second images, a single reference image for the first image can be generated and used as reference for detecting defects on the first image. The single reference image can be generated based on the multiple second images, e.g., by averaging, or weighted averaging, or calculating median of the pixel values in the one or more second images, or any other suitable approaches of deriving a composite or average image from multiple images.

In some embodiments, the first image and the one or more second images can be captured (e.g., by the inspection unit) respectively for one or more detection channels (e.g., bright field (BF) channel and gray field (GF) channel in the case of an optical inspection tool). Accordingly the image processing process as will be described in details below with respect to blocks 206 and 208 can be performed respectively for each detection channel and the defect determination process as will be described in details below with respect to block 212 will be based on the one or more detection channels.

Information indicative of DOI (i.e., defect to be detected as per user's interest, as described above with reference to FIG. 1) and noise (including non-DOI and/or random noise, as described above with reference to FIG. 1) can be obtained. According to certain embodiments, a first set of predefined first descriptors and a second set of predefined second descriptors can be received (204) (e.g., by the I/O interface 126). Each predefined first descriptor in the first set can be indicative of pixel value distribution in a first image block associated therewith and represent a type of DOI. Each predefined second descriptor in the second set can be indicative of pixel value distribution in a second image block associated therewith and represent a type of noise. The first image block and the second image block are reference image blocks that are used to represent or illustrate the pixel value distribution indicated by the first and second descriptors. Each of the first and second image blocks can have a size of a predefined number of pixels. In some cases, the first and second image blocks have the same size of number of pixels. In some other cases, the first image block can have a first size of a first predefined number of pixels, and the second image block can have a second size of a second predefined number of pixels. According to certain embodiments, the first descriptors and the second descriptors can be predefined by users according to the type of DOIs to be inspected and the type of noises to be filtered out. In some cases, these descriptors can be defined based on pixel value distribution learnt from previous inspection results. For example, previous inspection results (e.g., from a review tool) can reveal true DOIs whose patterns can be learnt and represented by certain pixel value distribution.

It is to be noted that the first set and the second set used herein are not limited by the number of descriptors included in each set and can each include one or multiple predefined descriptors, depending on the number of types of DOIs to be detected, and the number of types of noises to be excluded from the detection results. As described above, the noise referred to herein includes both non-DOI(s) and random noise(s). Noises can be of various types. By way of example, one type of noise is detector noise. For instance, the detector noise can be Spontaneous Emission (SE) noise.

Figure 4:
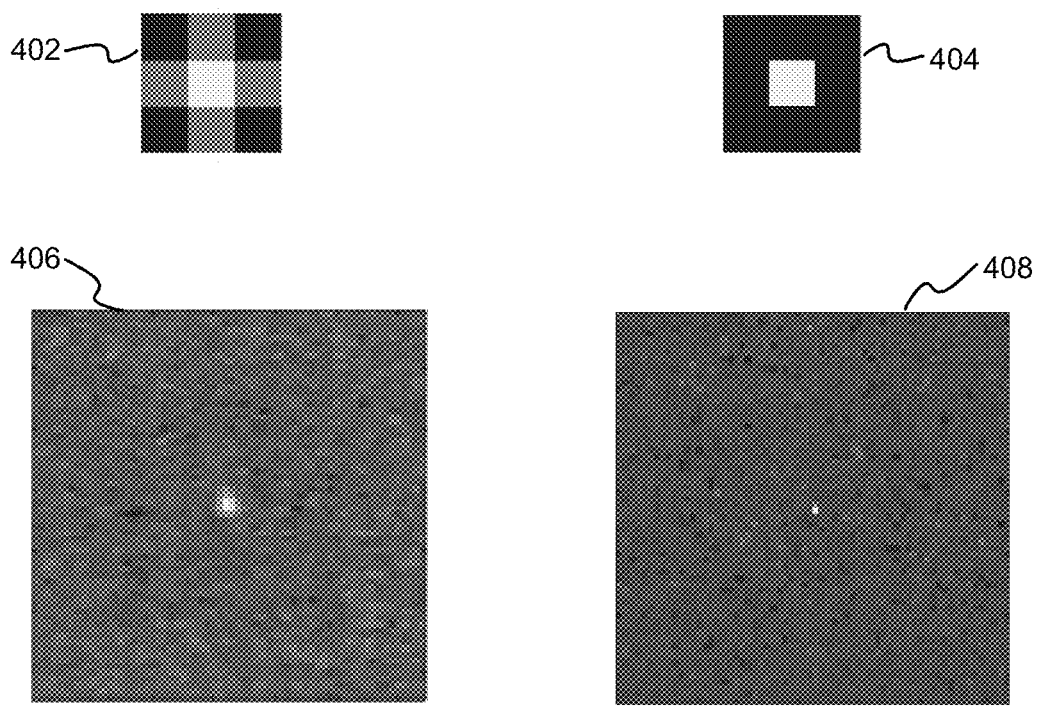
FIG. 4 illustrates examples of a predefined first descriptor representing a type of DOI and a predefined second descriptor representing a type of noise and corresponding difference images in the presence of a DOI and in the presence of SE noise in accordance with certain embodiments of the presently disclosed subject matter.

Turning now to FIG. 4, there are illustrated examples of a predefined first descriptor representing a type of DOI and a predefined second descriptor representing a type of noise and corresponding difference images in the presence of a DOI and in the presence of SE noise in accordance with certain embodiments of the presently disclosed subject matter.

For illustrative purposes, there is shown an example of a predefined first descriptor 402 representing a type of DOI. The exemplary first descriptor 402 is illustrated as pixel value distribution in a 3-pixel by 3-pixel first image block (i.e., the first image block associated with the first descriptor). As shown, the exemplary first descriptor 402 indicates a pixel value distribution of a two-dimensional Gaussian kernel (e.g., a wide Gaussian kernel). In the illustrated image block it is shown as a gradual change of pixel values from the center pixel to the pixels immediately adjacent thereto (i.e., the upper, lower, left and right pixels of the center pixel).

In comparison, there is also shown an example of a predefined second descriptor 404 representing a type of noise. Specifically, in the present example, the type of noise is Spontaneous Emission (SE) noise. SE noise refers to a type of system noise related to the detectors. The exemplary second descriptor 404 is illustrated as pixel value distribution in a 3-pixel by 3-pixel second image block (i.e., the second image block associated with the second descriptor). As shown, the exemplary second descriptor 404 indicates a pixel value distribution of a two-dimensional Gaussian kernel (e.g., a narrow Gaussian kernel). In the illustrated image block it is shown as a single pixel event, e.g., a very high measurement in the center pixel. This type of noise can generate false alarms in the detection process therefore affecting the detection results.

It is to be noted that the image block representations of the first and second descriptors as shown in FIG. 4 are for illustration purposes only and should not be construed to limit the present disclosure in any way. Accordingly other kinds of representation or illustration of the first and second descriptors can be implemented in addition or in lieu of the above. For example, the first descriptor and/or the second descriptor can be represented in the form of a vector containing the pixel values in the associated image block.

It is also to be noted that FIG. 4 only shows one example of pixel value distribution for each of the first and second descriptor. Other suitable pixel distributions can also be used to represent various types of DOIs to be detected and noises to be excluded from the detection results. By way of example, each of the first set of predefined first descriptors can be indicative of pixel value distribution in a two-dimensional kernel selected from a group comprising: a Gaussian kernel, a polynomial kernel, a uniform kernel, and an exponential kernel, etc. Each of the second set of predefined second descriptors can be indicative of pixel value distribution in a two-dimensional kernel selected from a group comprising: a Gaussian kernel, a polynomial kernel, a uniform kernel, and an exponential kernel, etc. Any other suitable kernels that are not listed above but can be used to represent pixel value distribution of defects and/or noises can also be employed in addition or in lieu of the above.

Referring back to FIG. 2 now, upon obtaining the first image and the one or more second images, as described with reference to block 202, these images can be processed (e.g., by the Image processing module 104 of the processing unit 102, as illustrated in FIG. 1). Specifically, at least one difference image can be generated (206) based on difference between pixel values of the first image and pixel values derived from the one or more second images (i.e., reference images). At least one third image (also referred to as a grade image hereinafter) corresponding to the at least one difference image can be generated (208). The generation of the at least one third image can comprise computing (210) a value for each given pixel of at least part of the at least one difference image based on the first set of predefined first descriptors, the second set of predefined second descriptors, and surrounding pixels centered around the given pixel.

In order to generate (206) a difference image for a first image, difference between pixel values of the first image and corresponding pixel values derived from the one or more reference images are used. In some cases, when there is only one reference image, the derived pixel values can be the pixel values of the one reference image, and the difference image can be generated based on difference between pixel values of the first image and the reference image. Accordingly a third image can be generated corresponding to the difference image. In the case that there are multiple reference images, at least one difference image can be generated and accordingly at least one third images can be generated. By way of example, the corresponding pixel values of the multiple reference images can be combined and averaged (not limited to the averaging method that can be applied), and difference between the pixel values of the first image and the averaged pixel values derived from the multiple reference images can constitute the pixel values of the difference image. In this case, one third image can be generated corresponding to the difference image. By way of another example, multiple difference images can be generated each based on a difference between pixel values of the first image and corresponding pixel values of a respective reference image of the multiple reference images. In this case, multiple third images can be generated corresponding to the multiple difference images.

According to certain embodiments, the pixel values of the difference image can be further processed with respect to a predefined difference normalization factor. The predefined difference normalization factor can be determined based on behavior of normal population of pixel values and can be used to normalize the pixel values of the difference image. By way of example, the normalize pixel value can be calculated as a ratio between a corresponding pixel value of the difference image and the predefined difference normalization factor.

According to certain embodiments, an adaptive imaging operation can be applied in the process of generating a difference image and a third image, for the purposes of dealing with noises occurred in the first image and/or the one or more second images. The noises can include noises caused by different variations, such as, color variation, variations of the specimen, e.g., process variation, etc. The noises can also include noises generated during inspection by the inspection unit. Specifically, the difference image can be generated based on a corrected difference between pixel values of the first image and pixel values derived from the one or more second images, giving rise to a corrected difference image so as to compensate the aforementioned noises, i.e., noises occurred in the first image and/or the one or more second images. Accordingly a corresponding third image is generated based on corresponding pixel values in the corrected difference image and a predefined difference normalization factor.

According to certain embodiments, in order to generate (208) a third image (i.e., grade image) corresponding to a difference image, for each given pixel of at least part of the at least one difference image, a pixel value is computed (210) based on the first set of predefined first descriptors, the second set of predefined second descriptors, and surrounding pixels centered around the given pixel, the computed pixel values constituting at least part of the third image. In some embodiments, the computation can be performed for each pixel of the entire different image. In some other embodiments, the computation can be performed for a part of the difference image. For example, the computation can be performed for all the pixels except for the edge pixels of the difference image.

In some embodiments, the computation can be performed by computing a value for the given pixel in accordance with a predefined formula or equation related to a first set of block operations each using a predefined first descriptor and at least part of the surrounding pixels and a second set of block operations each using a predefined second descriptor and at least part of the surrounding pixels. By way of example, the block operations used herein can be selected from a group comprising: convolution operation, calculation of correlations between blocks, and calculation of image attributes, etc. By way of example, the predefined formula can be a polynomial formula, as will be exemplified further below with reference to FIG. 4.

As described above, in some cases, the first image block associated with a first descriptor and the second image block associated with a second descriptor can have the same size of predefined number of pixels. In such cases, the computation (210) of pixel value of the third image can comprise: selecting, on the difference image, a surrounding image block constituted by surrounding pixels centered around the given pixel, the surrounding image block having the same size as the first image block and the second image block; and computing a value for the given pixel in accordance with a predefined formula related to a first set of block operations each using a predefined first descriptor and the surrounding pixels and a second set of block operations each using a predefined second descriptor and the surrounding pixels.

In some other cases, the first image block and the second image block can have different sizes. For instance, the first image block has a first size of a first predefined number of pixels, and the second image block has a second size of a second predefined number of pixels. In such cases, the computation (210) of pixel value of the third image can comprise: selecting, on the difference image, a first surrounding image block and a second surrounding image block each constituted by surrounding pixels centered around the given pixel, the first surrounding image block having the same size as the first image block, the second surrounding image block having the same size as the second image block; and computing a value for the given pixel in accordance with a predefined formula related to a first set of block operations each using a predefined first descriptor and surrounding pixels in the first surrounding image block and a second set of block operations each using a predefined second descriptor and surrounding pixels in the second surrounding image block.

Turning now to FIG. 4 again, there are shown an example of a difference image (or part thereof) 406 in the presence of a DOI in the corresponding first image, and an example of a difference image (or part thereof) 408 in the presence of SE noise in the corresponding first image. It can be seen that the pixel distribution of the DOI in 406 and the pixel distribution of the SE noise in 408 are consistent with the pixel distribution representing the corresponding first and second descriptors 402 and 404, as described above. Assuming a given difference image comprising both a DOI as presented in 406 and a SE noise as presented in 408, when generating the third image corresponding to the difference image, the computation of each pixel value of the third image can be in accordance with e.g., a polynomial formula. In the present example, the first image block and the second image block have the same size (i.e., 3-pixel by 3-pixel). Thus a surrounding image block having the same size (i.e., 3-pixel by 3-pixel) and centered around each given pixel can be selected. The polynomial formula can relate to a first block operation using the first descriptor (i.e., 402) and the surrounding pixels in the surrounding image block and a second block operation using the second descriptor (e.g., 404) and the same surrounding pixels. For illustrative purposes, both first block operation and second block operation can be selected as convolution operations, and the polynomial formula can be written as, e.g.:

$$G = a_{2,0}x^2 + a_{1,1}xy + a_{0,2}y^2 + a_{1,0}x + a_{0,1}y + a_{0,0}$$

wherein G is the computed pixel value for a given pixel in the third image, x is the value of the pixel after convolution of the surrounding image block of the given pixel with the first descriptor, and y is the value of the pixel after convolution of the surrounding image block of the given pixel with the second descriptor, and $a_{i,j}$ are coefficients. The values of the coefficients can be based on one or more factors including (but not limited to): statistical models of the DOIs and the noise, which can be derived from the inspection tool physics or learned from previous measurements, and the level of noise reduction as needed, etc.

It is to be noted that the specific polynomial formula used and the selection of block operations etc. are illustrated as non-limiting examples and should not be construed to limit the present disclosed subject matter in any way. Accordingly, other types of formulas and block operations can be used in addition or in lieu of the above.

It is to be noted that the generation of difference image and grade image as described above are illustrated as non-limiting examples and are for the purpose of illustration only and should by no means be construed as limiting the present disclosure in any way. Other alternative ways of calculating pixel values for a difference image and/or a grade image can be applied in addition or in lieu of the above.

The presence of defect candidates in the first image can be determined (212) (e.g., by the defect determination module 106 of the processing unit 102, as illustrated in FIG. 1) based on the at least one third image and a predefined threshold. In some embodiments, the threshold can be determined based on a required amount of defect candidates (e.g., a budget). By way of example, any pixel in the third image with a value that exceeds the predefined threshold can be determined as an indication of presence of defect candidates in the corresponding first image. Since certain types of noises are filtered out from the inspection result, a more sensitive threshold can be used thereby enabling the system to reveal more DOIs which previously would be buried within the noises due to the weak or low signal level thereof as compared to the noises. Therefore, the present disclosed detection method is capable of increasing the level of sensitivity of detection for these defects.

According to certain embodiments, information of the defect candidates can be sent to a review tool or review unit (i.e., a high-resolution inspection unit) for further inspection, and information of defects detected by the review tool can be obtained to be used for refining definition of the first set of predefined first descriptors and the second set of predefined second descriptors.

Figure 3:
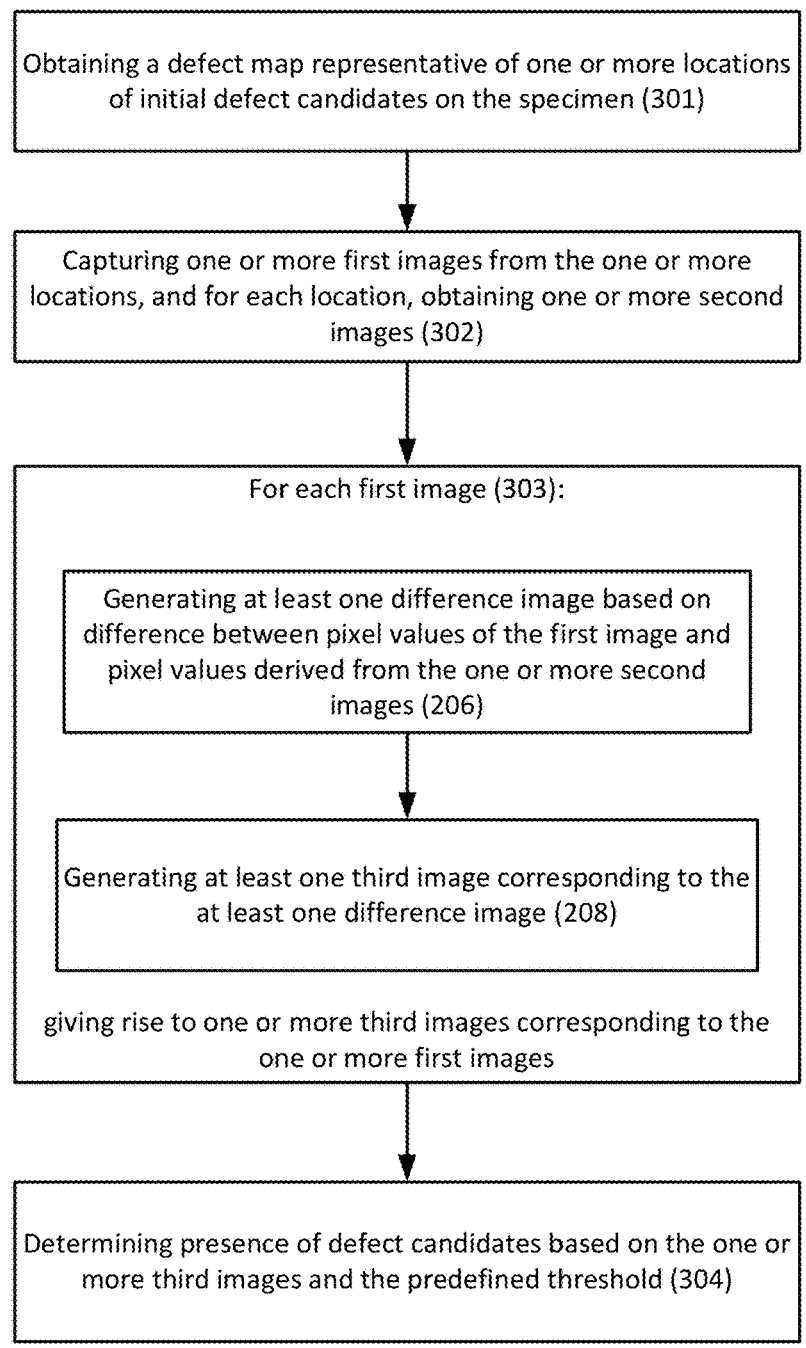
FIG. 3 illustrates another generalized flowchart of detecting defects on a specimen in accordance with certain embodiments of the presently disclosed subject matter.

Referring to FIG. 3 now, there is illustrated another generalized flowchart of detecting defects on a specimen in accordance with certain embodiments of the presently disclosed subject matter.

According to certain embodiments, the above proposed method can be applied on initial inspection results. By way of example, a defect map representative of one or more locations of initial defect candidates on the specimen can be obtained (301). In some embodiments, the defect map can be obtained from an inspection unit (e.g., from the inspection unit 120 or a different inspection unit operatively connected to system 100). One or more first images from the one or more locations indicated in the defect map can be captured (302) (e.g., by the inspection unit 120), and for each location, one or more second images can be obtained. The generation of at least one difference image as described with respect to block 206, and the generation of at least one third image as described with respect to block 208 can be performed (303) for each first image, giving rise to one or more third images. The presence of defect candidates can be determined (304) based on the one or more third images and the predefined threshold, similarly as described with reference to block 212.

According to certain embodiments, prior to the generation of the difference image as described with reference to block 206, a given first image (i.e., inspection image) and the one or more reference images thereof can be registered to be aligned. Some differences between the positions of the inspection image and the reference images are likely to occur for various reasons—scanning conditions (e.g. illumination) as well as imperfections, shifts and outright errors in the scanning process, manufacture errors, and so forth. The registration process can be implemented according to any suitable method of registration algorithms known in the art.

According to certain embodiments, in the case where the first image and the one or more second images are captured respectively for one or more detection channels (e.g., BF channel and GF channel), the generating a difference image and a third image as described above with reference to blocks 206 and 208 are performed respectively for each detection channel, giving rise to respective third images (e.g., a BF average third image and a GF average third image). The determination (212) of presence of defect candidates on the specimen can be based on the respective third images and a predefined composite defect threshold composed of a combination of one or more defect thresholds of the one or more detection channels.

It is to be noted that although certain operations are described and illustrated in a certain order (as shown in the flow chart of FIGS. 2 and 3), the teachings of the presently disclosed subject matter are not bound by the order of the steps in the flow chart illustrated therein. Some of the illustrated operations can occur out of the illustrated order. For example, the operation of receiving the first and second descriptors as described in 204 can be performed anywhere before block 208, e.g., prior to block 202 or after block 206.

It is also noted that whilst the flow charts illustrated in FIG. 2 and FIG. 3 are described with reference to elements of system 100, this is by no means binding, and the operations can be performed by elements other than those described herein.

It is to be further noted that in some cases the image processing and defect detection processes can be performed upon the scanning/inspection (e.g., by the inspection unit) of the specimen being completed. In some other cases the scanning of the specimen and the image processing process can be performed in parallel. By way of example, once the inspection unit scanned part of the specimen, the image processing operation, or at least part thereof, can be performed on the obtained inspection images, while at the same time the inspection unit can move on to scan subsequent part of the specimen.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable storage medium tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. A computerized system of detecting defects on a specimen, the system comprising:
   an inspection unit configured to capture a first image from a first die of the specimen and obtain one or more second images;
   an I/O interface configured to receive: i) a first set of predefined first descriptors each indicative of pixel value distribution in a first image block associated therewith and representing a type of defect of interest (DOI), and ii) a second set of predefined second descriptors each indicative of pixel value distribution in a second image block associated therewith and representing a type of noise; and
   a processing unit operatively connected to the inspection unit and the I/O interface, the processing unit comprising a memory and a processor operatively coupled thereto, wherein:
   the processing unit is configured to:
   generate at least one difference image based on difference between pixel values of the first image and pixel values derived from the one or more second images;
   generate at least one third image corresponding to the at least one difference image, comprising, computing a value for each given pixel of at least part of the at least one difference image based on the first set of predefined first descriptors, the second set of predefined second descriptors, and surrounding pixels centered around the given pixel; and
   determine presence of defect candidates in the first image based on the at least one third image and a predefined threshold.

2. The computerized system according to claim 1, wherein the one or more second images include one or more images captured from one or more second dies, or a simulated image representing the first die.

3. The computerized system according to claim 1, wherein the computing comprises computing a value for the given pixel in accordance with a predefined formula related to a first set of block operations each using a predefined first descriptor and at least part of the surrounding pixels and a second set of block operations each using a predefined second descriptor and at least part of the surrounding pixels.

4. The computerized system according to claim 3, wherein the predefined formula is a polynomial formula.

5. The computerized system according to claim 3, wherein the block operations are convolution operations.

6. The computerized system according to claim 1, wherein the first image block has a size of a predefined number of pixels, the second image block has the same size as the first image block, and wherein the computing comprises:
   i) selecting, on the at least one difference image, a surrounding image block each constituted by surrounding pixels centered around the given pixel, the surrounding image block having the same size as the first image block, and
   ii) computing a value for the given pixel in accordance with a predefined formula related to a first set of block operations each using a predefined first descriptor and the surrounding pixels and a second set of block operations each using a predefined second descriptor and the surrounding pixels.

7. The computerized system according to claim 1, wherein the first image block has a first size of a first predefined number of pixels, the second image block has a second size of a second predefined number of pixels, and wherein the computing comprises:
   i) selecting, on the at least one difference image, a first surrounding image block and a second surrounding image block constituted by surrounding pixels centered around the given pixel, the first surrounding image block having the same size as the first image block, the second surrounding image block having the same size as the second image block; and ii) computing a value for the given pixel in accordance with a predefined formula related to a first set of block operations each using a predefined first descriptor and surrounding pixels in the first surrounding image block and a second set of block operations each using a predefined second descriptor and surrounding pixels in the second surrounding image block.

8. The computerized system according to claim 1, wherein the inspection unit is further configured to obtain a defect map representative of one or more locations of initial defect candidates on the specimen, and capture one or more first images from the one or more locations, and for each location, obtain one or more second images, wherein the generating at least one difference image and generating at least one third image are performed for each first image, giving rise to one or more third images corresponding to the one or more first images; and wherein the determining presence of defect candidates is based on the one or more third images and the predefined threshold.

9. The computerized system according to claim 1, wherein the noise includes a non-DOI defect.

10. The computerized system according to claim 1, wherein the type of noise includes detector noise.

11. The computerized system according to claim 10, wherein the detector noise is Spontaneous Emission (SE) noise.

12. The computerized system according to claim 1, wherein the specimen is selected from a group comprising: a wafer, a reticle, a mask, an integrated circuit and a flat panel display.

13. The computerized system according to claim 1, wherein each of the first set of predefined first descriptors is indicative of pixel value distribution in a two-dimensional kernel selected from a group comprising: a Gaussian kernel, a polynomial kernel, a uniform kernel, and an exponential kernel.

14. The computerized system according to claim 1, wherein each of the second set of predefined second descriptors is indicative of pixel value distribution in a two-dimensional kernel selected from a group comprising: a Gaussian kernel, a polynomial kernel, a uniform kernel, and an exponential kernel.

15. The computerized system according to claim 1, wherein the first set of predefined first descriptors and the second set of predefined second descriptors are defined based on pixel value distribution learnt from previous inspection results.

16. The computerized system according to claim 1, wherein the at least one difference image is generated based on a corrected difference between pixel values of the first image and pixel values derived from the one or more second images, giving rise to at least one corrected difference image so as to compensate noises occurred in the first image, and wherein the at least one third image is generated based on the at least one corrected difference image.

17. The computerized system according to claim 1, wherein the predefined threshold is determined based on a required amount of defect candidates.

18. The computerized system according to claim 1, wherein the processing unit is further configured to send information of the defect candidates to a review machine for further inspection, and obtain information of defects detected by the review machine to be used for refining definition of the first set of predefined first descriptors and the second set of predefined second descriptors.

19. A computerized method of detecting defects on a specimen, the method comprising:

capturing, by an inspection unit, a first image from a first die of the specimen and obtaining one or more second images;

receiving, by an I/O interface: i) a first set of predefined first descriptors each indicative of pixel value distribution in a first image block associated therewith and representing a type of defect of interest (DOI), and ii) a second set of predefined second descriptors each indicative of pixel value distribution in a second image block associated therewith and representing a type of noise;

generating, by a processing unit operatively connected to the inspection unit and the I/O interface, at least one difference image based on difference between pixel values of the first image and pixel values derived from the one or more second images;

generating, by the processing unit, at least one third image corresponding to the at least one difference image, comprising, computing a value for each given pixel of at least part of the at least one difference image based on the first set of predefined first descriptors, the second set of predefined second descriptors, and surrounding pixels centered around the given pixel; and determining, by the processing unit, presence of defect candidates in the first image based on the at least one third image and a predefined threshold.

20. A non-transitory computer readable storage medium tangibly embodying a program of instructions that, when executed by a computer, causing the computer to perform a method of detecting defects on a specimen, the method comprising:

obtaining a first image from a first die of the specimen and obtaining one or more second images;

receiving: i) a first set of predefined first descriptors each indicative of pixel value distribution in a first image block associated therewith and representing a type of defect of interest (DOI), and ii) a second set of predefined second descriptors each indicative of pixel value distribution in a second image block associated therewith and representing a type of noise;

generating at least one difference image based on difference between pixel values of the first image and pixel values derived from the one or more second images;

generating at least one third image corresponding to the at least one difference image, comprising, computing a value for each given pixel of at least part of the at least one difference image based on the first set of predefined first descriptors, the second set of predefined second descriptors, and surrounding pixels centered around the given pixel; and determining presence of defect candidates in the first image based on the at least one third image and a predefined threshold.

* * * * *